United States Patent

Toth et al.

[11] Patent Number: 6,118,840
[45] Date of Patent: Sep. 12, 2000

[54] METHODS AND APPARATUS TO DESENSITIZE INCIDENT ANGLE ERRORS ON A MULTI-SLICE COMPUTED TOMOGRAPH DETECTOR

[75] Inventors: Thomas L. Toth, Brookfield; Hui David He, Waukesha; Gurmen O. Erdogan, Shorewood; Bing Shen, Milwaukee, all of Wis.

[73] Assignee: General Electric Company, Milwaukee, Wis.

[21] Appl. No.: 09/008,912

[22] Filed: Jan. 20, 1998

[51] Int. Cl.⁷ .......................................................... A61B 6/03
[52] U.S. Cl. .................................. 378/19; 378/4; 250/367
[58] Field of Search ................................. 378/4, 19, 147, 378/7; 250/367, 368, 363.01

[56] References Cited

U.S. PATENT DOCUMENTS

| | | | |
|---|---|---|---|
| 4,159,424 | 6/1979 | Kingsley | 250/483.1 |
| 4,180,737 | 12/1979 | Kingsley | 250/367 |
| 5,757,878 | 5/1998 | Dobbs et al. | 378/19 |
| 5,781,606 | 7/1998 | Dobbs et al. | 378/19 |

*Primary Examiner*—David P. Porta
*Assistant Examiner*—Drew A. Dunn
*Attorney, Agent, or Firm*—Armstrong Teasdale; Christian G. Cabou; Phyllis Y. Price

[57] ABSTRACT

Scintillators having a geometric configurations that substantially prevent x-ray beams from passing entirely through a gap between adjacent scintillators are described. More particularly, if the scintillators are cut on an angle to form parallelogram or trapezoidal shapes, or if the detector module is tilted in the x-ray beam z-axis, an x-ray beam will not pass through a non-scintillating gap between adjacent scintillators over the range of focal spot positions. Such scintillators have an increased geometric efficiency compared to known scintillator constructions.

11 Claims, 4 Drawing Sheets

METHODS AND APPARATUS TO DESENSITIZE INCIDENT ANGLE ERRORS ON A MULTI-SLICE COMPUTED TOMOGRAPH DETECTOR

FIELD OF THE INVENTION

This invention relates generally to computed tomography (CT) imaging and more particularly, to a detector configuration in a CT system.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object.

Each detector element of the array produces a separate electrical signal that is a measurement of the beam attenuation at the detector location. Particularly, each x-ray detector element typically includes a collimator for collimating x-ray beams received at the detector cell, and a scintillator is located adjacent the collimator. The scintillator includes a plurality of scintillating elements, and adjacent scintillators are separated by a non-scintillating gap. Photodiodes are positioned adjacent the scintillator elements and generate electrical signals representative of the light output by the scintillator elements. The attenuation measurements from all the detector cells are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Multislice CT systems are used to obtain data for an increased number of slices during a scan. Known multislice systems typically include detectors generally known as 2-D detectors. With such 2-D detectors, a plurality of detector cells form separate columns, or channels, and the columns are arranged in rows. Each row of detectors forms a separate slice. For example, a two slice detector has at least two rows of detector cells, and a four slice detector has at least four rows of detector cells. During a multislice scan, multiple rows of detector cells are simultaneously impinged by the x-ray beam, and therefore data for several slices is obtained.

In a multislice detector, each cell is subjected to X-rays from a range of angles depending on its Z-axis location. In one configuration for a helical scan, the angular range is about ±1 degree at the extreme Z axis edges of the detector. Because the detector is made up of scintillating segments separated by small non-scintillating gaps, the signal will be at a minimum when the X-ray beam is generally perpendicular to the scintillators. The signal increases as the angle of the x-ray beam increases from perpendicular because the perpendicular X-ray beams have the lowest geometric collection efficiency. Such low geometric efficiency results since angled X-rays are presented with a smaller effective non-scintillating gap than perpendicular X-rays.

Further, since each channel (or sets of channels built as modules), do not have identical gap configurations or Z-axis positions within the detector, there is a phase difference between the minimum gain points. Additionally, the focal spot typically moves in the Z-axis up to 1.0 mm due to the thermal expansion and centrifugal forces interacting with gravity. This position change creates a change in incident angle by about 0.06 degrees. Due to the phase differences between the minimum gain points, differential channel gain variations of 0.2% or more can occur over the range of focal spot positions.

Third generation CT scanners may produce ring, band and center spot artifacts when differential gain errors exceed 0.02%. Differential gain values are calibrated and then corrected during image reconstruction. However, the variation in incident angle changes the differential gain during scanner operation and hence cannot be easily corrected with software algorithms.

It would be desirable to provide a scintillator construction that has increased geometric efficiency compared to known scintillator constructions. It also would be desirable to provide such a scintillator construction which does not increase the scintillator fabrication costs nor reduce dose efficiency of the system.

SUMMARY OF THE INVENTION

These and other objects may be attained by a scintillator which, in an exemplary embodiment, have a geometric configuration that substantially prevents x-ray beams from passing entirely through a gap between adjacent scintillator elements. More particularly, if the scintillator elements are cut on an angle to have parallelogram or trapezoidal geometric shapes, or if the detector module is tilted in the x-ray beam z-axis, an x-ray beam will not pass through a non-scintillating gap between adjacent scintillator elements over the range of focal spot positions. The amount of angulation can be reduced if the non-scintillating gap is made as narrow as reasonably practical. In an alternative embodiment, and rather than selecting a particular geometric configuration for the scintillator, or in combination therewith, attenuating wires are positioned between and overlap a portion of adjacent scintillator elements.

The above described scintillators have an increased geometric efficiency compared to known scintillator constructions. Such scintillator construction also does not significantly increase the scintillator fabrication costs and improves the dose efficiency of the system.

DETAILED DESCRIPTION OF THE DRAWINGS

Figure 1:
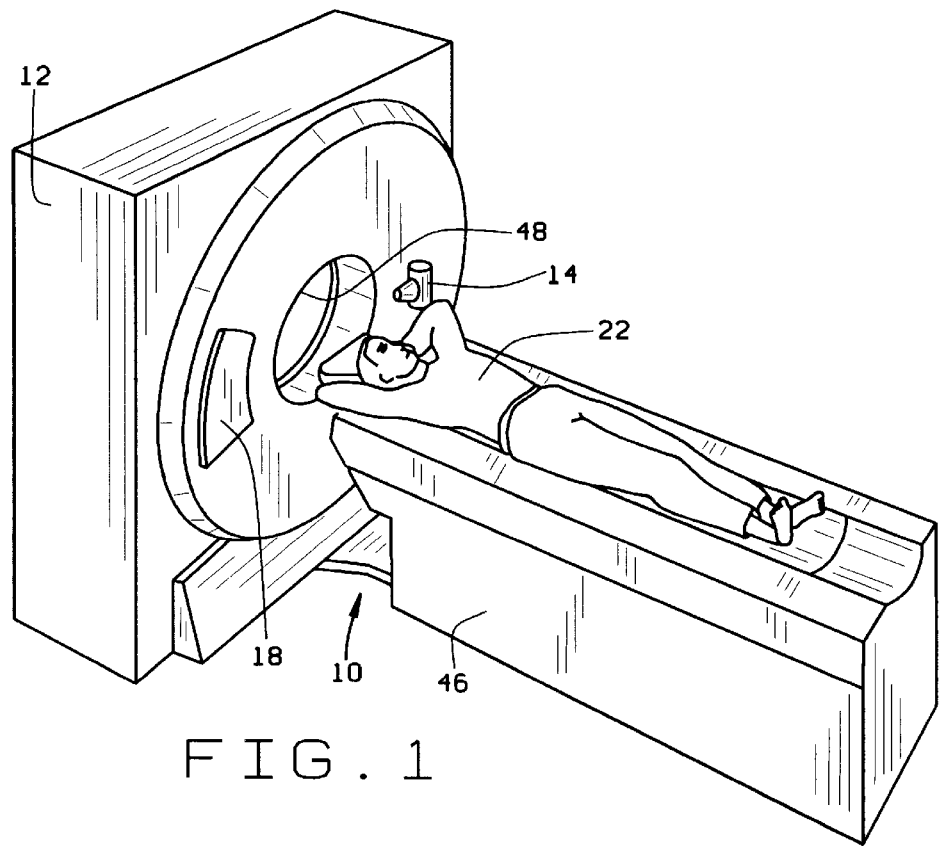
FIG. 1 is a pictorial view of a CT imaging system.
Figure 2:
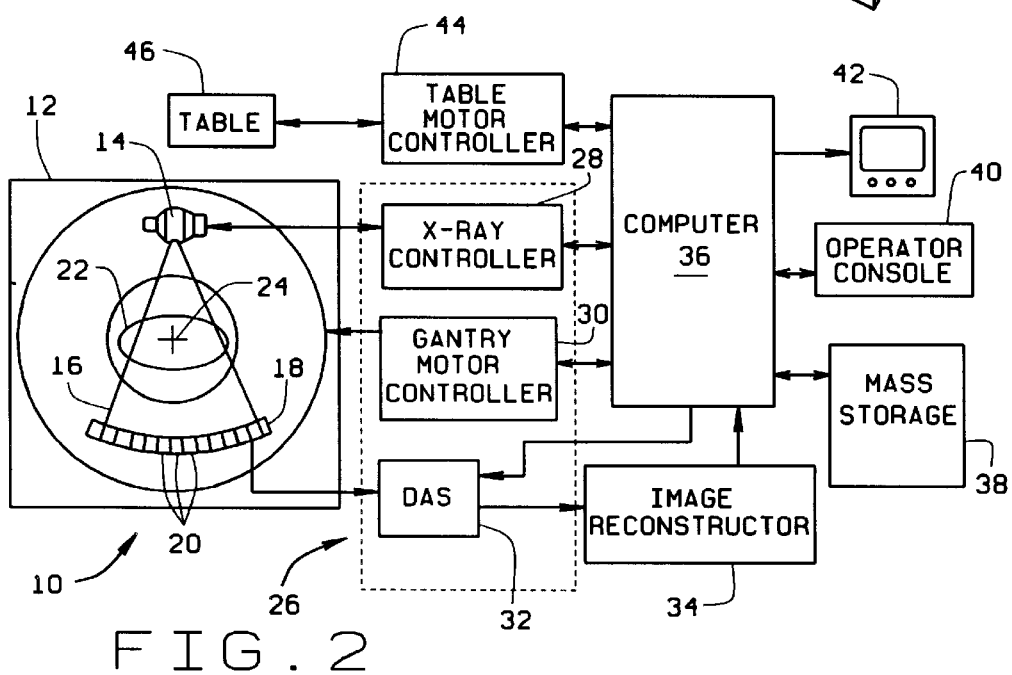
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

As explained above, each detector cell, or element, 18 of array 20 produces a separate electrical signal that is a measurement of the beam attenuation at the detector location. Particularly, each x-ray detector element 18 typically includes a collimator for collimating received x-ray beams, and a scintillator is located adjacent the collimator. Adjacent scintillator elements are separated by a non-scintillating gap. Photodiodes are positioned adjacent the scintillator elements and generate electrical signals representative of the light output by the scintillators. The attenuation measurements from all detector elements 18 are acquired separately to produce a transmission profile.

Each cell is subjected to X-rays from a range of angles depending on its Z-axis location. In one configuration for a helical scan, the angular range is about ±1 degree at the extreme Z axis edges of the detector. If the detector is made up of scintillating segments separated by small non-scintillating gaps, the signal will be at a minimum when the X-ray beam is generally perpendicular to the scintillators. The signal increases as the scintillator elements are angled with respect to the x-ray beams. The perpendicular X-ray beams have the lowest geometric collection efficiency due to the X-rays that pass through the non-scintillating gap. Angled scintillators present a smaller effective non-scintillating gap than perpendicular x-rays.

Generally, and with respect to the detector arrays described below and constructed in accordance with the present invention, the scintillator elements are configured or positioned to have minimum effective non-scintillating gaps. By providing a minimum effective non-scintillating gap, the incident angle errors are minimized.

Figure 3:
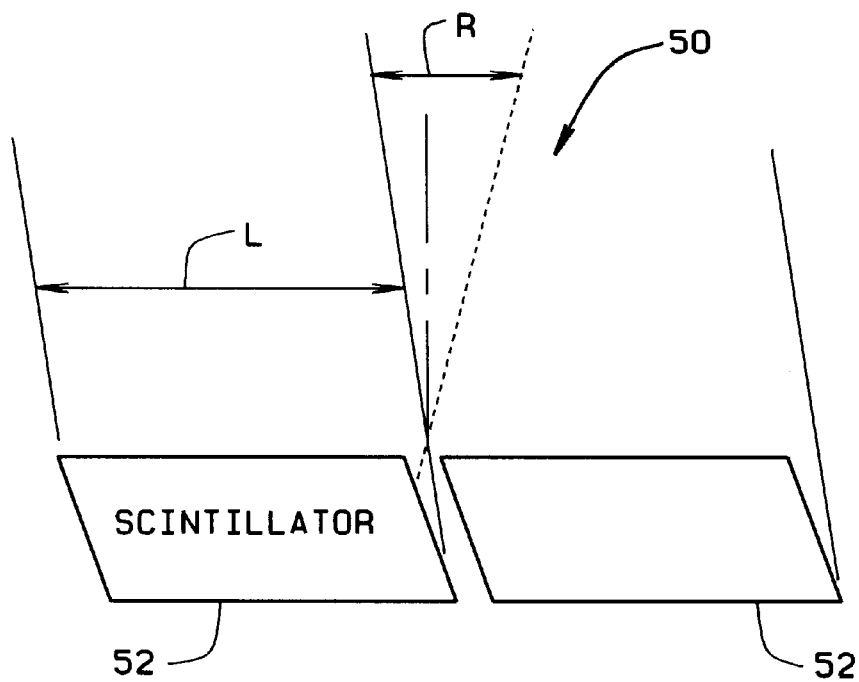
FIG. 3 is a schematic illustration of adjacent parallelogram shaped scintillators.

More particularly, FIG. 3 is a schematic illustration of a portion of an array 50 having adjacent scintillator elements 52 with parallelogram geometric shapes. Each scintillator element 52 has a surface length L which provides that at least one scintillator element 52 intercepts an x-ray beam within a range R of possible x-ray beam angles. Scintillator elements 52 having parallelogram geometric shapes can be fabricated using known cutting tools used to fabricate the known rectangular shaped scintillators.

Figure 4:
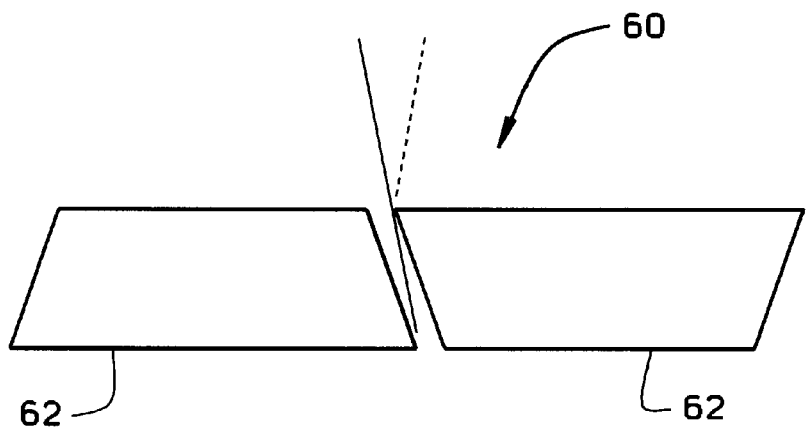
FIG. 4 is a schematic illustration of adjacent trapezoidal shaped scintillators.

FIG. 4 is a schematic illustration of a portion of an array 60 having adjacent scintillator elements 62 with trapezoidal geometric shapes. As with scintillator elements 52, at least one scintillator element 62 intercepts an x-ray beam within a range of possible x-ray beam angles. Adjacent scintillator elements 62 are inverted with respect each other so that scintillators 62 can be positioned close to each other to minimize any non-scintillating gap. Scintillator elements 62 having trapezoidal geometric shapes can be fabricated using known cutting tools used to fabricate the known rectangular shaped scintillators.

Figure 5:
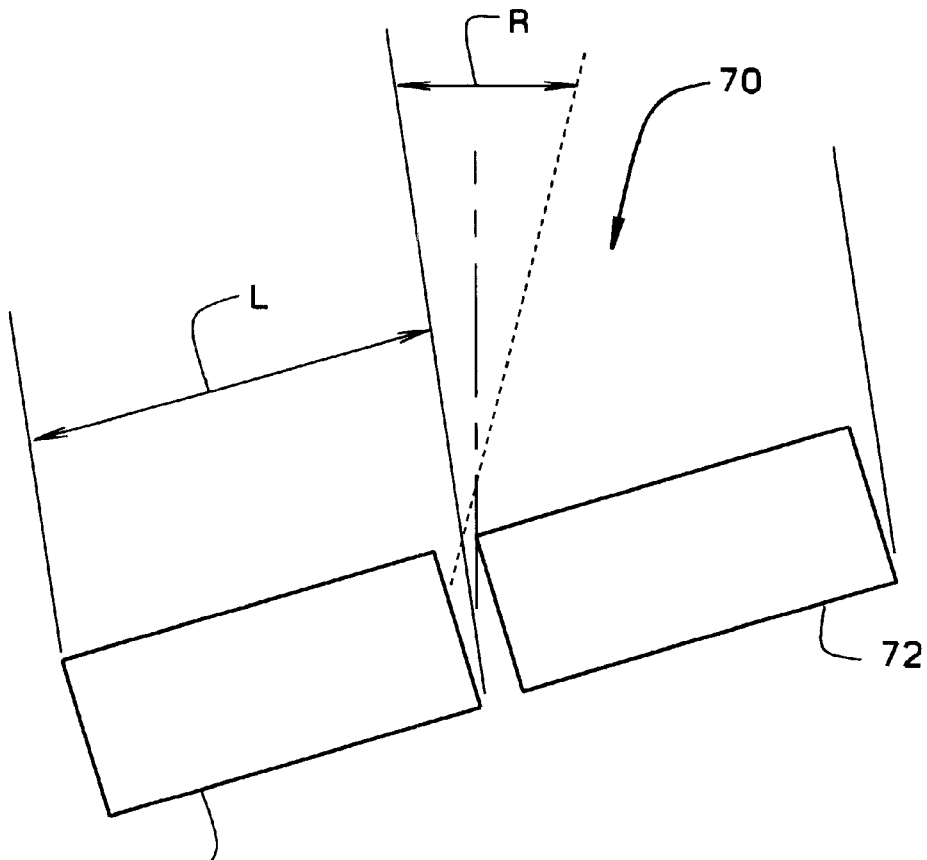
FIG. 5 is a schematic illustration of angled scintillators.

FIG. 5 is a schematic illustration of an array 70 having angled scintillator elements 72 with rectangular geometric shapes. Scintillator elements 72 are oriented so that at least one scintillator element 72 intercepts an x-ray beam within a range of possible x-ray beam angles. Specifically, scintillator elements 72 are mounted at an angle with respect to a plane perpendicular to x-ray beams generated by the imaging system. Scintillator elements 72 can be mounted at such an angle by modifying the mounting surfaces of known detectors to have an angled mounting surface. The amount of angulation can be small if the non-scintillating gap is as narrow as reasonably practical.

Figure 6:
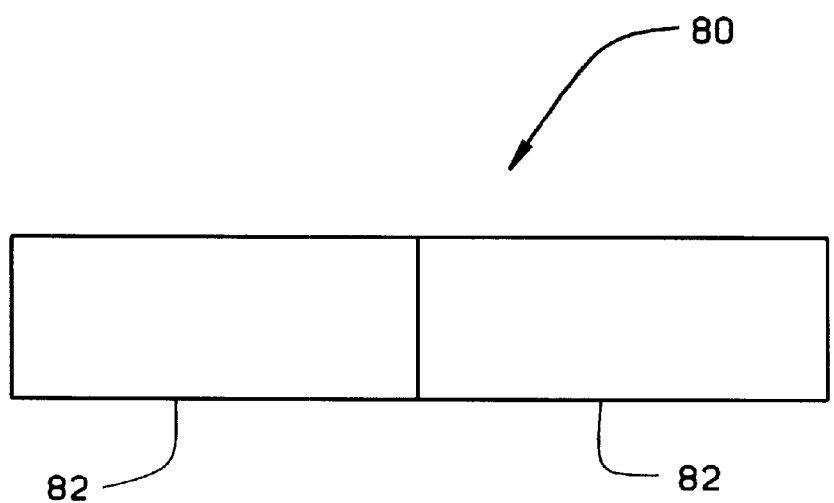
FIG. 6 is a schematic illustration of closely spaced scintillators.

FIG. 6 is a schematic illustration of an array 80 having closely spaced scintillator elements 82. In known systems, the scintillator elements are spaced apart by about 0.1 mm. By minimizing non-scintillating gap 84 (i.e., less than 0.1 mm), at least one scintillator element 82 intercepts an x-ray beam within most of the range of possible x-ray beam angles.

The above described scintillator configurations have an increased geometric efficiency compared to known scintillator constructions. Such scintillator configurations also do not significantly increase the scintillator fabrication costs and improve the dose efficiency of the system.

Figure 7A:
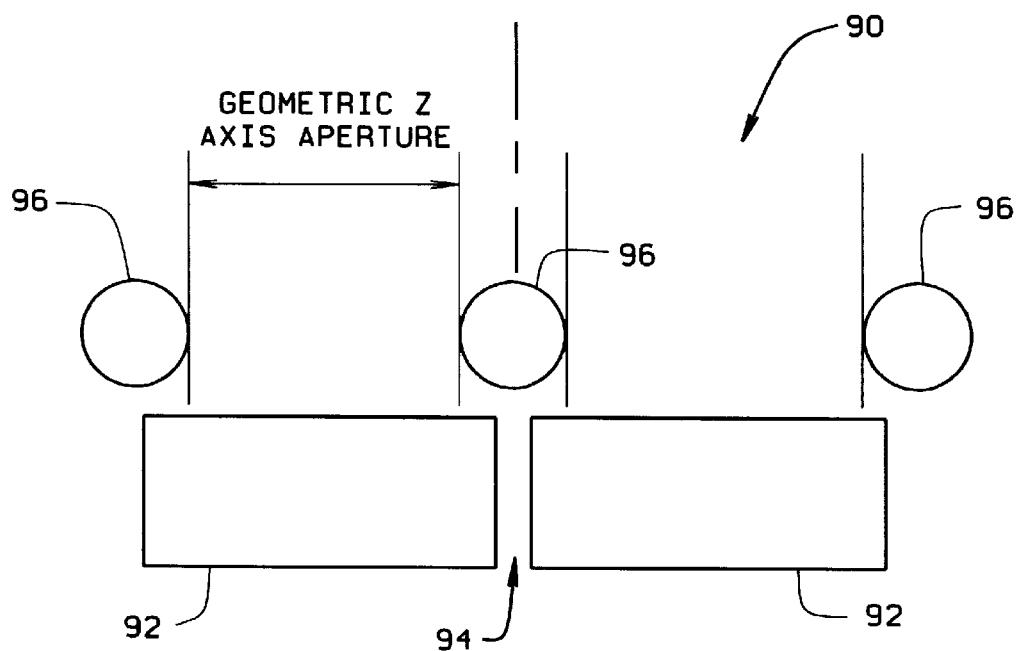
FIGS. 7a and 7b are schematic illustrations of adjacent scintillators with attenuating wires positioned therebetween.
Figure 7B:
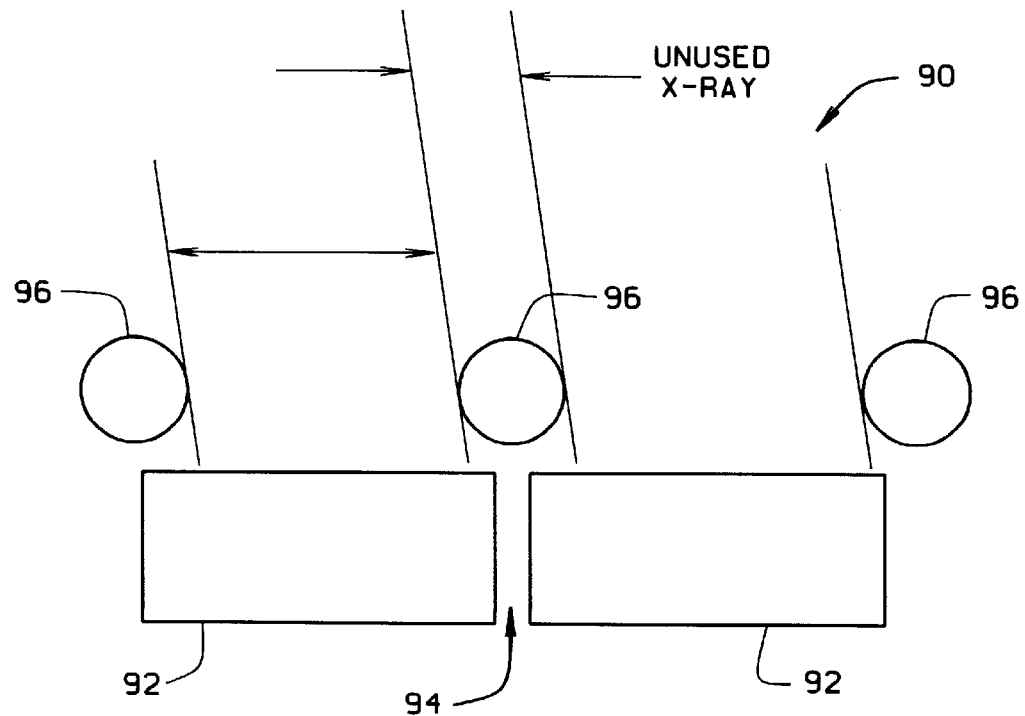

FIGS. 7a and 7b are schematic illustrations of an array 90 having adjacent scintillator elements 92 with rectangular geometric shapes. A nonscintillating gap 94 is located between adjacent scintillator elements 92. Attenuating wires 96 are positioned over gaps 94 and over a portion of scintillator elements 92. With small wires 96 (e.g., 0.28 mm), the z-axis alignment relative to wires 96 must be precise (about 10 micrometers). Small wires 96 minimize unused patient dose (low geometric dose efficiency).

As shown in FIG. 7a, and when the x-ray beam is generally perpendicular to scintillator elements 92, wires 96 prevent the x-ray beam from impinging upon the edges of scintillator elements 92 and prevent the x-ray beam from being transmitted between gaps 94. Similarly, and as shown in FIG. 7b, when the angle of the x-ray beam changes from perpendicular, wires 96 still prevent the x-ray beam from being transmitted between gaps 94.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Accordingly, the spirit and scope of the invention are to be limited only by the terms of the appended claims.

What is claimed is:

1. A system for obtaining data measured signals and for producing a tomographic image of an object in a tomographic scan, said system comprising a multi-slice detector array comprising a plurality of detector cells, at least some of said detector cells having adjacent scintillator elements extending in a direction perpendicular to an imaging plane and further having a geometric shape configured to have minimum effective non-scintillating gaps in a direction parallel to the imaging plane between said adjacent scintillator elements.

2. A system in accordance with claim 1 wherein said adjacent scintillator elements each have an upper surface and a side surface, said adjacent scintillator elements configured so that x-rays impinging said detector array from a range of incident angles impinge said upper surfaces of said adjacent scintillator elements and at least one of said side surfaces of said adjacent scintillator elements in said gap between said adjacent scintillator elements.

3. A system in accordance with claim 2 wherein said range of incident angles includes +1 degree relative to the imaging plane.

4. A system in accordance with claim 2 wherein said adjacent scintillator elements have a parallelogram geometric cross-section.

5. A system in accordance with claim 2 wherein said adjacent scintillator elements have a trapezoidal geometric cross-section.

6. A system in accordance with claim 1 wherein said adjacent scintillator elements are mounted at an angle with respect to a plane perpendicular to x-ray beams generated by said system.

7. A system in accordance with claim 6 wherein said adjacent scintillator elements have a rectangular geometric cross-section.

8. A system in accordance with claim 1 wherein said adjacent scintillator elements have a rectangular geometric cross-section and are less than 0.1 mm apart.

9. A system for obtaining data measured signals and for producing a tomographic image of an object in a tomographic scan, said system comprising a multi-slice detector array comprising a plurality of detector cells, at least some of said detector cells having adjacent scintillator elements extending in a direction perpendicular to an imaging plane and having gaps therebetween extending in a direction parallel to the imaging plane, and at least one attenuating wire aligned over an upper opening of at least one of said gaps.

10. A system in accordance with claim 9 comprising a plurality of attenuating wires, at least some of said respective attenuating wires aligned over an upper opening of said gaps.

11. A system in accordance with claim 9 wherein said attenuating wire has a diameter of about 0.28 mm.

* * * * *